United States Patent [19]

Lowe

[11] 4,411,156

[45] Oct. 25, 1983

[54] ODOR TESTING APPARATUS

[76] Inventor: Henry E. Lowe, 21725 Allegheny St., Cassopolis, Mich. 49031

[21] Appl. No.: 231,867

[22] Filed: Feb. 5, 1981

[51] Int. Cl.³ .................... G01N 1/22; G01N 33/24; G01N 33/48

[52] U.S. Cl. .................... 73/432 R; 73/23; 73/863; 73/863.81

[58] Field of Search ............ 73/23, 863.33, 432 T; 119/16, 17; 52/234, 173 R; 98/29, 43 R, 43 A, 43 B, 43 C

[56] References Cited

U.S. PATENT DOCUMENTS

| | | | |
|---|---|---|---|
| 1,721,942 | 7/1929 | Booher | 119/16 |
| 2,644,934 | 7/1953 | Grant | 73/863.33 |
| 2,837,912 | 6/1958 | Moncrieff | 73/432 T |
| 3,357,257 | 12/1967 | Herndon et al. | 73/863.33 |
| 3,623,792 | 11/1971 | Meyer | 52/234 |
| 3,736,792 | 6/1973 | Poulsen | 73/863.33 |

OTHER PUBLICATIONS

40 Ways to Plan Bathrooms, American Builder, vol. 73, Issue 8, Aug. 1951, pp.92-99.

*Primary Examiner*—S. Clement Swisher

*Attorney, Agent, or Firm*—Marmaduke A. Hobbs

[57] ABSTRACT

An apparatus for testing small animal litter in which a plurality of compartments are employed for living quarters for the small animals, such as cats, and for a container with litter to be tested, and these animal compartments are connected by conduits to a compartment for a tester to use to sniff the odor from any one of the animal compartments. Valves are preferably provided in the conduits, and controls for the valves extend externally of the apparatus so the valves can be operated separately by an operator without interfering with individual tests. Fans in or near the top of the compartments are used to circulate air through the animal compartments while the animals are living normally therein, and a fan is provided in the tester's compartment for drawing the air from any selected one of the animal compartments into and through the tester's compartment. Drains are preferably provided in the bottom of the compartments to permit water and other liquids to drain therefrom and to facilitate cleaning of the compartments. The compartments have doors and are preferably sufficiently large that a normal adult can stand erect therein.

15 Claims, 4 Drawing Figures

U.S. Patent Oct. 25, 1983 Sheet 1 of 2 4,411,156
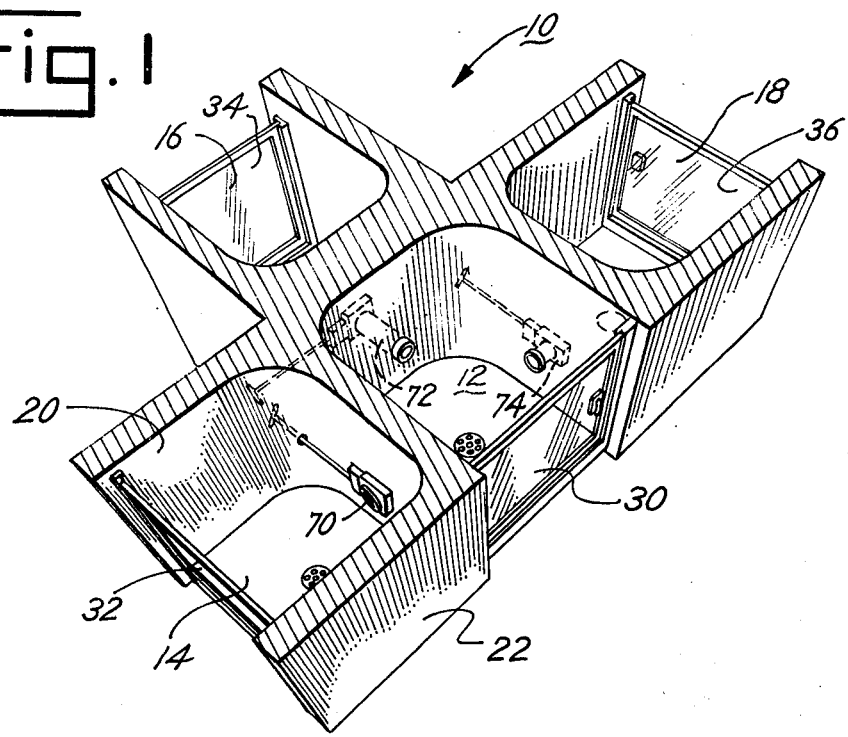
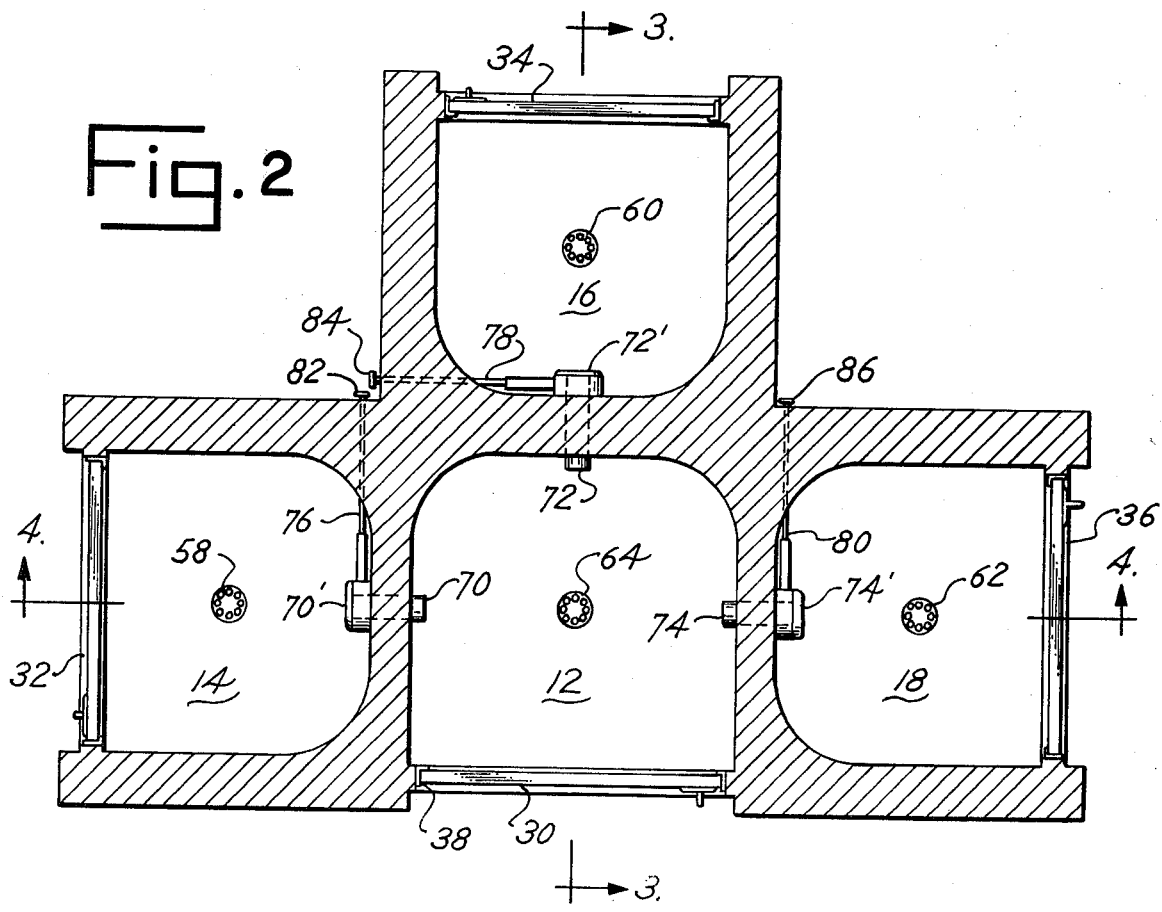

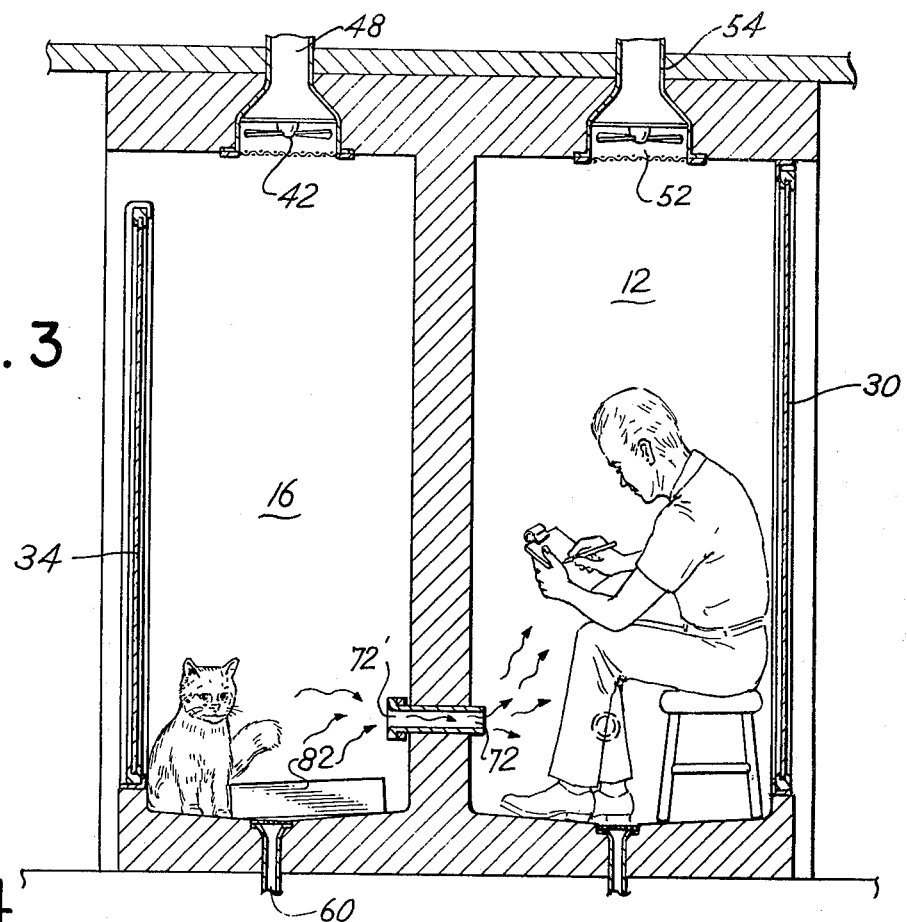
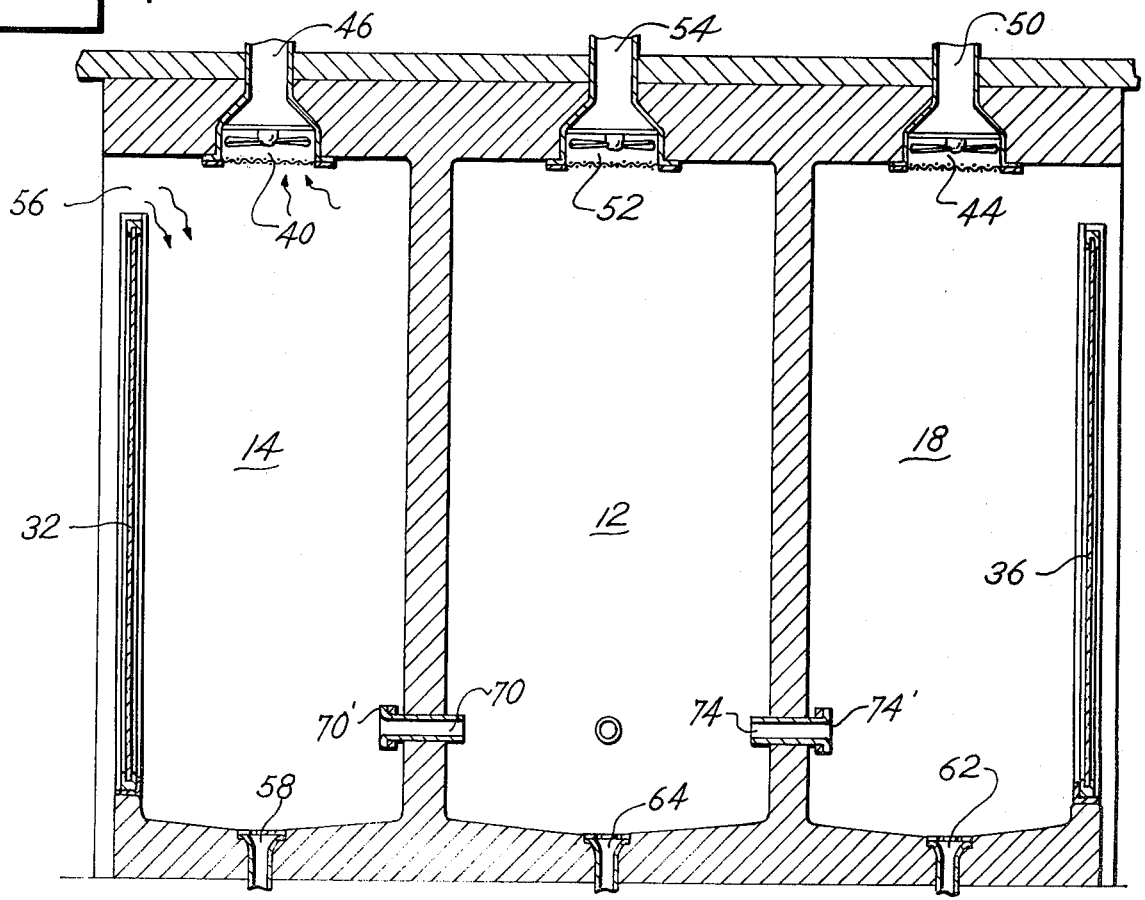

ODOR TESTING APPARATUS

BACKGROUND OF THE INVENTION

One of the principal problems encountered in the sale and use of litter for small animals, particularly cats, is suppressing the odor resulting from urine and feces buried and mixed with the litter as it is used daily by the animal. Since the litter, particularly for cats, is usually placed in a box, pan or the like, and is kept in the home where the cat will use it several times during the day, the waste creates an odor which permeates the room or other space where the container is located, and may create an unpleasant odor throughout the house. To eliminate the odor problem, odor masking or suppressant materials are often added to commercial litters in the form in which they are sold, and concentrated odor control preparations are available which can be added to the litter after the litter has been placed in the container for use by the cat. While some of these preparations used to mask or suppress odors are effective in varying degrees for a period of time, they diminish in effectiveness as the litter is exposed to the air in the container and may eventually become totally ineffective. One of the problems encountered in improving the odor suppressant or control products, and in determining the effectiveness of the products as they are used, is the lack of a means of establishing standards for comparison or even making a direct comparison among the various products available. Some products are exceptionally effective when initially released in the litter, while others are effective to a lesser degree over a longer period of time. Further, it has been difficult to determine the amount of odor control composition required to give optimum results for the normal period of use of the litter by the cat. Since the odor control compositions are generally relatively expensive, it is desirable not to add more of the material to the litter than the amount required to obtain satisfactory odor control for the normal use of the litter. This can only be accomplished reliably by testing and comparing the various compositions under normal or simulated normal conditions.

SUMMARY OF THE INVENTION

One of the principal objects of the present invention is to provide an apparatus which assists in testing various compositions for controlling the odor of animal litter and in comparing the odor suppressing capabilities of various types and brands of animal litter, and which will create and maintain conditions similar to those encountered during normal use of the litter. The primary, if not the only, method of testing the effectiveness of odor control compositions in animal litter and in making comparisons between various types and brands of litters, is by smell, using a person trained through experience to recognize acceptable and unacceptable odor conditions of the litter after it had been in use by an animal for predetermined periods of time.

The present invention relates to an apparatus for assisting in testing and comparing the odor characteristics of various litters and formulations of odor suppressants while the litter is in use under essentially normal animal living conditions. The apparatus includes a plurality of compartments in which the litters to be tested are placed, and in which animals are confined for normal living for preselected periods of time, and a compartment for a person who has developed a discriminating olfactory sense for variations in odor from used animal litter. The animal compartments are connected individually with the tester's compartment by separate conduits containing valves which can be opened and closed without the knowledge of the tester. One or more fans circulate the air or atmosphere of the animal compartments to and through the tester's compartment as the valves are opened and closed in the conduits from particular animal compartments. Since the tester is unaware of the brands or litter compositions in the various compartments, and of the valves being operated to connect a particular animal compartment with the tester's compartment, the tester can be objective in his opinions with respect to the quality or acceptability of the litters being tested with respect to their odors, and can make odor comparisons among the litters in the various animal compartments. The apparatus may contain any number of animal compartments, and one or more tester's compartments, and may be used to test a variety of materials other than litter.

BRIEF DESCRIPTION OF THE DRAWINGS

FIG. 1 is a perspective view of an animal litter odor testing apparatus embodying the present invention, the figure showing the apparatus with the top or ceiling removed therefrom in order to better illustrate the construction of the apparatus;

FIG. 2 is a horizontal cross sectional view of the apparatus shown in FIG. 1;

FIG. 3 is a vertical cross sectional view of the apparatus shown in FIGS. 1 and 2, the section being taken on line 3—3 of FIG. 2; and FIG. 4 is a vertical cross sectional view of the apparatus shown in the preceding figures, the section being taken on line 4—4 of FIG. 3.

Referring more specifically to the drawings, numeral 10 indicates generally the present apparatus, consisting of a tester's compartment and several compartments around the tester's compartment in which the animals and litter materials are placed for conducting tests. While the drawings illustrate an apparatus with three animal compartments, more or fewer compartments may be used. Although the apparatus is designed for testing the litter used by various small animals, it is primarily intended for testing litter for cats.

In the embodiment illustrated, the apparatus consists of a tester's compartment 12, and three animal compartments, 14, 16 and 18. The tester's and animal compartments are shown constructed as a single unit; however, they may be constructed as modules and assembled at the place of final installation. The internal walls 20 of each of the compartments may be of plastic or sheet metal material formed to the desired configuration, and the external walls 22 may be of the same material or may be of any other structural material such as gypsum board or the like. The internal walls may be of sufficient strength to be self supporting so that, except for appearance, the external walls need not be used. The tester's compartment is closed by a hinged door 30, and animal compartments 14, 16 and 18 are closed by hinged doors 32, 34 and 36, the doors being hinged along vertical edge 38 and opening outwardly so that the tester can easily enter his compartment and a caretaker can easily enter the animal compartments to care for the animals and litter being used therein. Compartments 14, 16 and 18 have exhaust fans 40, 42 and 44 in the entrance to ducts 46, 48 and 50, respectively, and the tester's compartment has an exhaust fan 52 in a duct 54. The fans draw most of the air into the animal compartments through space 56 above each of the doors of the animal compartments, and thence circulate it through the respective compartments and outwardly through the respective ducts. The fans in the animal compartments are normally operated most of the time while no testing is in progress involving any of the compartments in which an animal is living. The fan in the tester's compartment is normally operated only when a test is being conducted. In order to assist in cleaning the compartments and to dispose of any spillage of water or liquid food in the animal compartments, drains 58, 60 and 62 are provided in the bottom of animal compartments 14, 16 and 18. A similar drain 64 is placed in the bottom of the tester's compartment to facilitate cleaning of the compartment.

Compartments 14, 16 and 18 are connected to the tester's compartment by conduits 70, 72 and 74 with valves 70', 72' and 74' therein for controlling the air flow through the respective conduits, the valves having sliding valve elements controlled by rods 76, 78 and 80, respectively. The rods extend outwardly through the compartment walls and preferably are provided with handles 82, 84 and 86 to facilitate manipulation of the valves by the rods. The valves are opened and closed by pulling the rods outwardly and pushing them inwardly, respectively. Thus, any one of the compartments can be connected with the tester's compartment by manipulation of the respective valve, normally by someone positioned externally of the animal and tester compartments.

The compartments are preferably of sufficient height to permit a normal adult person to stand erect therein, and the doors are sufficiently large that ingress and egress from all the compartments are possible without the person having to stoop over. The doors preferably have glass windows which permit the caretaker to inspect the animals in the compartments of the apparatus. While the animal and tester compartments are shown constructed as an integral unit, they can be constructed as modules and assembled into a unit or arranged in a different pattern and/or separated from one another. In any arrangement, the animal compartments are connected to the tester's compartment by suitable conduits such as conduits 70, 72 and 74.

In the use and operation of the present animal litter testing apparatus, a cat and a box of litter 82 are placed in one or more of the confinement compartments, and the cats live several days in the compartments, eating, sleeping and using the litter box. For a normal test, two or more of the compartments are used in this manner so that a comparison can be made between different litters in the compartments. After the cats have lived in the compartments, usually for a day or more, and have used the litter, a test is ready to be made. The tester enters the testing compartment 12 and the operator outside the apparatus opens one of the valves 70', 72' or 74' without the tester knowing which one has been opened. The fan 52 in the top of the tester's compartment is turned on and the fan in the animal compartment from which the test is to be made is turned off. The air is thus drawn from the selected compartment, for example, compartment 16 through valve 72', and the connecting conduit into compartment 12 where a person experienced in detecting acceptable and unacceptable odor levels of the litter, sniffs the air and rates the litter with respect to odor on a prepared chart or scale. The operator outside the apparatus then closes valve 72' and opens one of the other valves where a cat has been confined with a filled litter box. While the change has been communicated to the tester, the particular compartment and the litter being tested have not been revealed. The tester makes a similar rating on a scale or chart for the second test. This procedure is continued from one to the other until all of the litters in the animal compartments have been tested as desired. Instruments such as rate of air flow, temperature and moisture content may be used to assist the tester in performing consistent tests for comparison from one litter to another. The test may be repeated from time to time for several days while the cats live in their respective compartments and use the litter boxes therein.

After a particular test has been completed, the fan 52 is turned off and the fans for the various animal compartments are turned on to maintain fresh air in the animal compartments for proper living conditions. More than one animal compartment is normally used, not only so that a single test can be made for any particular litter, but also so that comparisons can be made among various litters and/or additives for litters; however, under some circumstances it may be desirable to make a test on a single litter, and in that event, only one of the animal compartments would be used.

In the detailed description and in the drawings, the apparatus is described and illustrated with reference to testing odors from cat litter. However, the apparatus can be advantageously used to test odors of other materials, including human body, household and industrial deodorants, and the odors of foods and beverages. With these other materials, the apparatus is used in substantially the same manner as in testing litters.

While only one embodiment of the present animal litter odor testing apparatus has been described in detail herein, various changes and modifications may be made without departing from the scope of the invention.

I claim:

1. A structure for testing small animal litter, comprising a plurality of animal confinement compartments in which the animals live and consummate their daily functions and in which litter for animal waste is placed for use by the animals, a compartment for enclosing a person testing the odors of the litter in particular animal compartments, port means near the bottom of each animal compartment, separate air flow conduits connecting said port means with the odor tester compartment for drawing air from the lower portion of the animal compartment into the tester compartment, a valve means for controlling each of said conduits, a fan for creating a flow of air from said animal compartments through selected port means and conduits and into said tester compartment, and an access door through which a tester can enter the tester compartment without passing through an animal compartment.

2. A structure for testing small animal litter as defined in claim 1 in which an exhaust fan is provided in the upper portion of each of said animal compartments.

3. A structure for testing small animal litter as defined in claim 1 in which each of said animal compartments has a floor and drain therein for removing liquids spilled on the floor of the compartments.

4. A structure for testing small animal litter as defined in claim 2 in which each of said animal compartments has a drain therein for removing liquids spilled on the floor of the compartments.

5. A structure for testing small animal litter as defined in claim 1 in which said conduits connecting the animal compartments with the tester's compartment are positioned in the lower portion of the compartments and spaced upwardly from the bottom thereof.

6. A structure for testing small animal litter as defined in claim 2 in which said conduits connecting the animal compartments with the tester's compartment are positioned in the lower portion of the compartments and spaced upwardly from the bottom thereof.

7. A structure for testing small animal litter as defined in claim 1 in which said valve means for controlling each of said conduits has a control means extending externally of the compartment for the respective means.

8. A structure for testing small animal litter as defined in claim 6 in which said valve means for controlling each of said conduits has a control means extending externally of the compartment for the respective means.

9. A structure for testing small animal litter as defined in claim 1 in which said compartments are of a size sufficiently large to permit a normal adult to stand substantially erect, and each of said compartments has a door through which a person may enter and leave.

10. A structure for testing small animal litter as defined in claim 1 in which said fan for creating a flow of air from said animal compartments into the tester's compartment is disposed in said tester's compartment.

11. A structure for testing small animal litter as defined in claim 6 in which said fan for creating a flow of air from said animal compartments into the tester's compartment is disposed in the top of said tester's compartment.

12. A structure for testing odors of various materials, comprising a plurality of compartments for materials to be tested, each of said compartments having a port means in the lower portion thereof, a compartment for a person testing the odors of the material in particular compartments, separate air flow conduits communicating with said port means and connecting the odor tester's compartment with said material compartments near the bottom thereof for drawing air from the lower portion of the respective material compartment into the tester's compartment, a valve means for controlling each of said conduits, a fan for creating a flow of air from said material compartments through selected air flow conduits into said tester's compartment, and a door for access by a tester to the odor testing compartment without passing through any of said material compartments.

13. A structure for testing odors of various materials as defined in claim 12 in which said conduits connecting the material compartments with the tester's compartment are positioned in the lower portion of the compartments and spaced upwardly from the bottom thereof.

14. A structure for testing odors of various materials as defined in claim 12 in which said valve means for controlling each of said conduits has a control means extending externally of the compartment for the respective means.

15. A structure for testing odors of various materials as defined in claim 12 in which said compartments are of a size sufficiently large to permit a normal adult to stand substantially erect, and each of said compartments has a door through which a person may enter and leave.

* * * * *